United States Patent
Desmier et al.

(10) Patent No.: US 6,885,199 B2
(45) Date of Patent: Apr. 26, 2005

(54) FUEL SENSOR

(75) Inventors: Isabelle Desmier, Auburn Hills, MI (US); David Vanzuilen, Fremont, IN (US); Francois-Xavier Bernard, Corronsac (FR); Gerard Mouaici, Toulouse (FR)

(73) Assignee: Siemens VDO Automotive Corp., Auburn Hills, MI (US)

( * ) Notice: Subject to any disclaimer, the term of this patent is extended or adjusted under 35 U.S.C. 154(b) by 205 days.

(21) Appl. No.: 10/150,903

(22) Filed: May 17, 2002

(65) Prior Publication Data

US 2003/0020494 A1 Jan. 30, 2003

Related U.S. Application Data

(60) Provisional application No. 60/291,781, filed on May 17, 2001, provisional application No. 60/325,369, filed on Sep. 27, 2001, and provisional application No. 60/341,022, filed on Oct. 30, 2001.

(51) Int. Cl.[7] ............................................... G01R 27/26
(52) U.S. Cl. ...................... 324/663; 73/61.41; 73/61.43
(58) Field of Search ........................ 324/663; 73/61.43, 73/61.41

(56) References Cited

U.S. PATENT DOCUMENTS

| | | | |
|---|---|---|---|
| 4,426,616 A | 1/1984 | Maier | |
| 4,555,661 A | 11/1985 | Benson et al. | |
| 4,915,084 A | 4/1990 | Gonze | |
| 4,945,863 A | 8/1990 | Schmitz et al. | |
| 4,971,015 A | 11/1990 | Gonze | |
| 5,060,619 A | 10/1991 | Sakurai et al. | |
| 5,089,703 A | 2/1992 | Schoen et al. | |
| 5,103,184 A | 4/1992 | Kapsokavathis et al. | |
| 5,119,671 A | 6/1992 | Kopera | |
| 5,134,381 A | 7/1992 | Schmitz et al. | |
| 5,179,926 A * | 1/1993 | Ament | 123/494 |
| 5,216,409 A | 6/1993 | Ament et al. | |
| 5,230,322 A | 7/1993 | Curran et al. | |
| 5,231,358 A | 7/1993 | Kapsokavathis et al. | |
| 5,255,656 A | 10/1993 | Rader et al. | |
| 5,301,542 A | 4/1994 | Meitzler et al. | |
| 5,361,035 A | 11/1994 | Meitzler et al. | |
| 5,367,264 A | 11/1994 | Brabetz | |
| 5,416,425 A | 5/1995 | Mouaici | |
| 5,503,004 A | 4/1996 | Agar | |
| 5,594,163 A | 1/1997 | Suzuki | |
| 5,717,339 A | 2/1998 | Murphy et al. | |
| 5,945,831 A | 8/1999 | Sargent et al. | |
| 6,578,416 B1 * | 6/2003 | Vogel et al. | 73/304 C |
| 6,712,503 B2 * | 3/2004 | Lin et al. | 374/45 |
| 2002/0040593 A1 * | 4/2002 | Schaefer et al. | 73/61.43 |
| 2002/0065582 A1 * | 5/2002 | Morrison et al. | 700/286 |
| 2003/0189969 A1 * | 10/2003 | Lin et al. | 374/54 |

FOREIGN PATENT DOCUMENTS

| | | | | |
|---|---|---|---|---|
| DE | 4312236 A1 * | 10/1993 | | F02D/41/00 |
| DE | 19938790 | 2/2001 | | |
| GB | 2 210 459 A | 6/1989 | | |

OTHER PUBLICATIONS

Patent Cooperation Treaty, International Search Report mailed Aug. 26, 2002.

* cited by examiner

Primary Examiner—Charles H. Nolan, Jr.

(57) ABSTRACT

A fuel sensor (20) includes a single capacitor (22) that operates in two different modes to obtain capacitance and conductance information when a fuel mixture flows between the electrodes (24, 26) of the capacitor. Two different oscillators (180, 182) are selectively used to obtain the conductance and capacitance information. In a disclosed embodiment, a capacitor includes an outer electrode (24) that is received around an inner electrode (26) such that there is a spacing between the electrodes through which the fuel flows. The fuel acts as a dielectric of the capacitor allowing the conductance and capacitance measurements to be made. The inventive fuel sensor can be readily incorporated into a variety of locations within a vehicle fuel supply system depending on the needs of a particular situation. In one example, a portion of the fuel rail (132) is used as one of the electrodes of the capacitor.

27 Claims, 8 Drawing Sheets

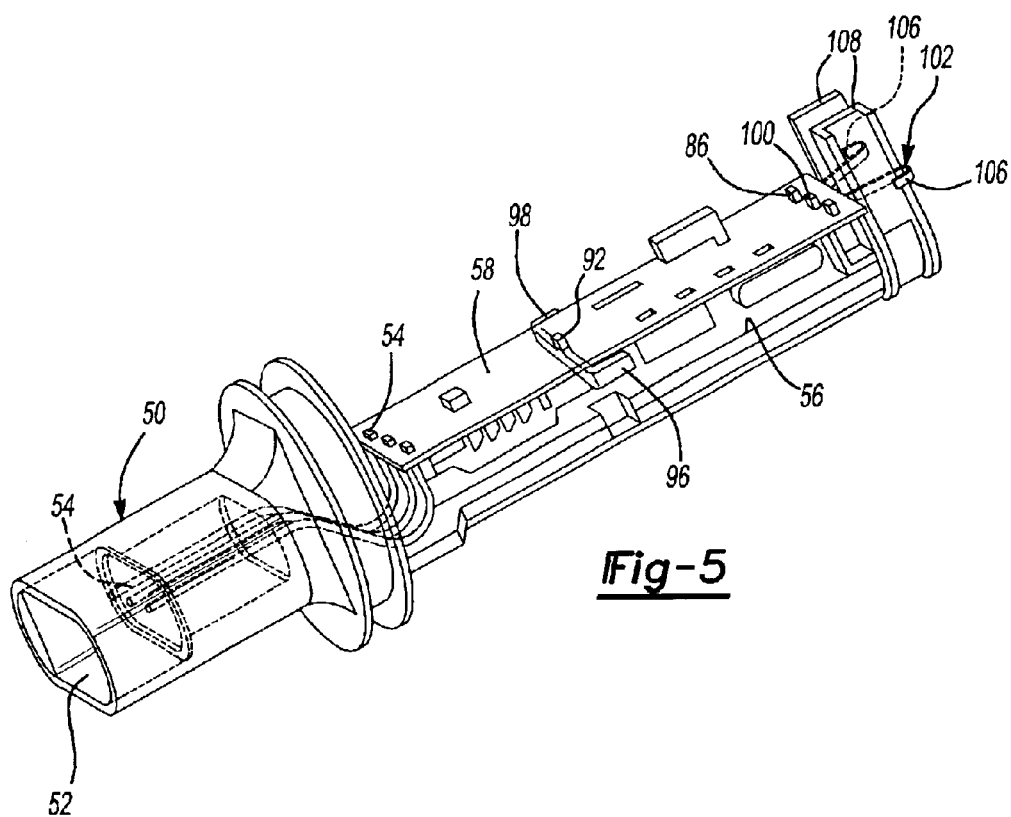
*Fig-5*
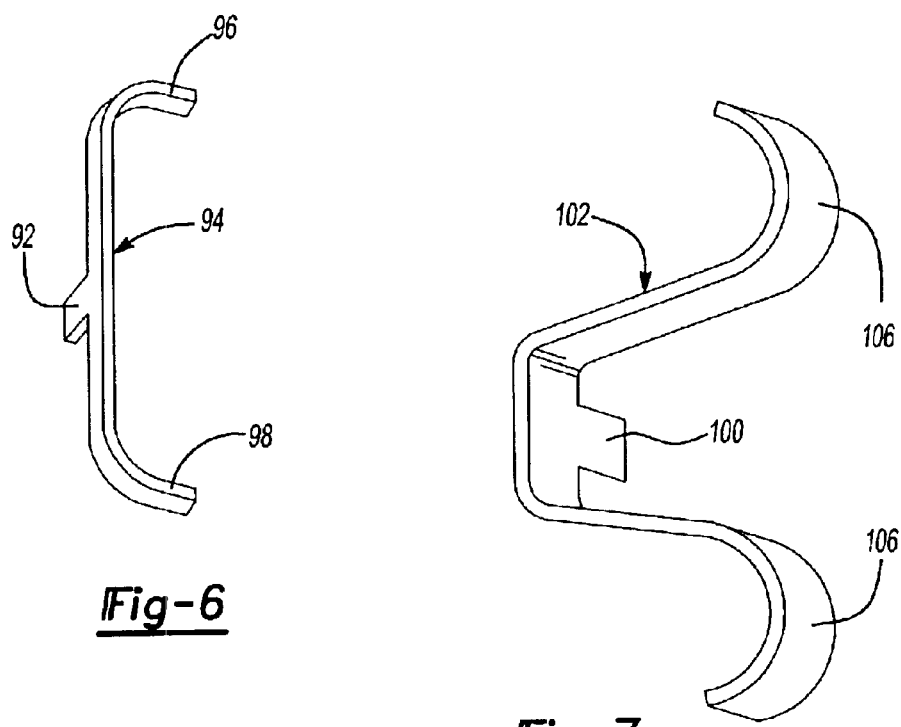
*Fig-6*
*Fig-7*

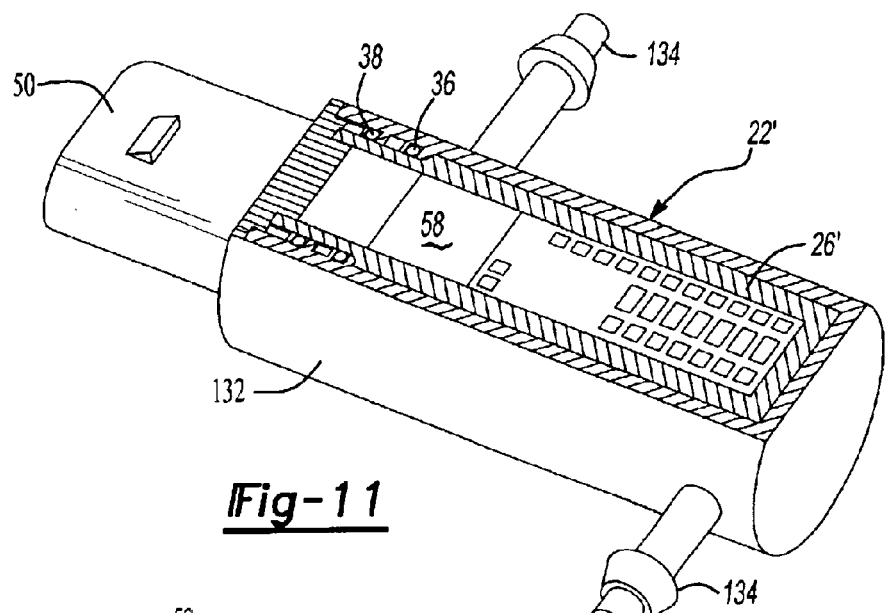
Fig-11
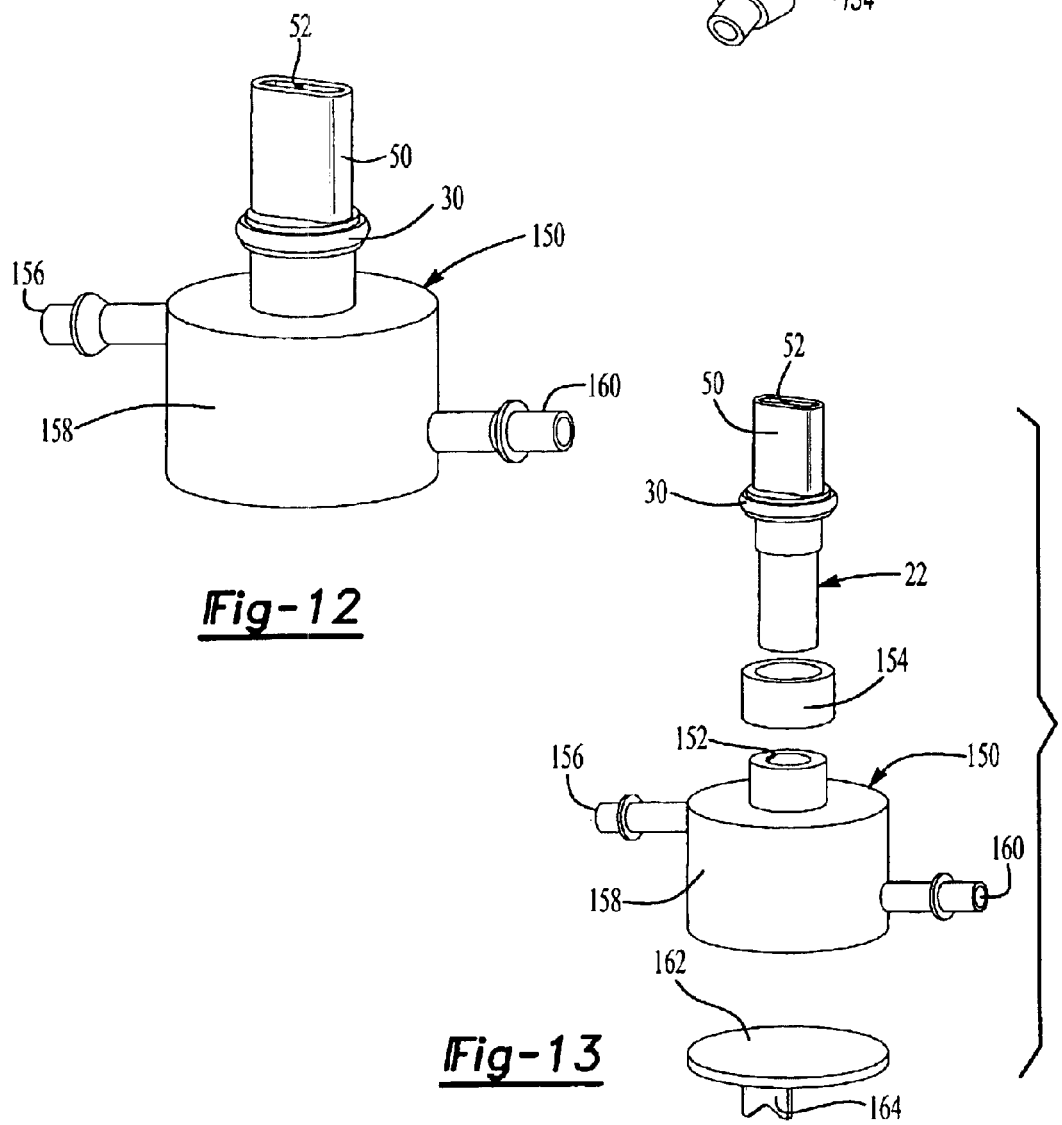
Fig-12
Fig-13

FUEL SENSOR

CROSS REFERENCE TO RELATED APPLICATIONS

This application claims priority to U.S. Provisional Application Nos. 60/291,781, which was filed on May 17, 2001; 60/325,369, which was filed on Sep. 27, 2001; and 60/341,022, which was filed on Oct. 30, 2001.

BACKGROUND OF THE INVENTION

1. Technical Field

This invention generally relates to fuel sensors. More particularly, this invention relates to a fuel sensor arrangement having a single capacitor that is used in two different modes to determine desired characteristics of a fluid such as a fuel mixture.

2. Description of the Prior Art

A variety of fuel sensors are known. Fuel sensors typically are used to determine the content of a fuel mixture within a fuel system of a vehicle. Some sensors are capable of determining the content of the fuel mixture such as a ratio or proportion of alcohol to gasoline within the fuel. Depending on the determined ratio, the ignition timing and fuel quantity supplied by fuel injectors may be adjusted by a suitable fuel flow control system.

It is known that the relative permittivity of gasoline differs from that of alcohol because of the different oxygen levels within each. Alcohol and gasoline also have different conductivity. Accordingly, the relative alcohol content of a fuel mixture is a well-defined function of the fluid's relative permittivity, temperature and conductivity.

Known sensors take advantage of these known characteristics of fuel mixtures and utilize the electrical properties of the fuel contents to make a determination regarding alcohol level within a fuel, for example. Sample patents in this field of endeavor include U.S. Pat. Nos. 4,945,863 and 5,367,264. Each of these patents show approaches to providing a fuel sensor that utilizes the electrical properties of the fluid for making fuel content determinations.

While the current approaches have proven satisfactory, those skilled in the art are always striving to make improvements. For example, packaging constraints on vehicle systems continuously cause an emphasis to be placed upon minimizing the size of components and maximizing the convenience of integrating them into vehicle systems. Additionally, cost savings are always a concern to automotive suppliers.

This invention addresses the need for providing a more economical and more convenient approach to fuel sensing technology.

SUMMARY OF THE INVENTION

In general terms this invention is a fuel sensor that utilizes a single capacitor operated in two different modes for determining the conductivity and permittivity of a fuel mixture to provide information regarding the contents of the fuel mixture.

In one example, the fuel sensor has a generally cylindrical portion that is readily inserted into a selected location as part of a vehicle fuel supply system. In a preferred embodiment, the fuel sensor body is effectively plugged into a corresponding opening on a selected portion of the fuel supply system.

The capacitor of the fuel sensor has a first, generally cylindrical electrode that is at least partially surrounded by the other electrode. The fuel mixture flows between the electrodes so that the appropriate conductivity and permittivity information can be determined. The capacitor effectively operates in two different modes (using two different oscillators in one example) so that the permittivity and conductivity measurements are made.

The sensor measurements can then be made available to another controller on the vehicle that adjusts the timing and fuel supply as necessary to compensate for the contents of the fuel mixture.

The many features and advantages of the various embodiments of this invention will become apparent to those skilled in the art from the following detailed description of the currently preferred embodiments. The drawings that accompany the detailed description can be briefly described as follows.

BRIEF DESCRIPTION OF THE DRAWINGS

FIG. 5 schematically illustrates selected portions of the embodiment of FIG. 2 showing selected details of an example arrangement for supporting electronics within the fuel sensor.

FIG. 6 schematically illustrates one example electrical connector spring useful with one example embodiment of this invention.

FIG. 7 illustrates another example electrical connector spring designed according to this invention.

FIG. 11 schematically illustrates, in partially cut-away, perspective view, another alternative arrangement of capacitor components in a fuel sensor assembly designed according to this invention.

FIG. 12 schematically illustrates an alternative embodiment of this invention where the fuel sensor is provided with a separate housing that is adapted to be incorporated into a fuel line.

FIG. 13 is an exploded view of the embodiment of FIG. 12.

DETAILED DESCRIPTION OF THE PREFERRED EMBODIMENTS

Figure 1:
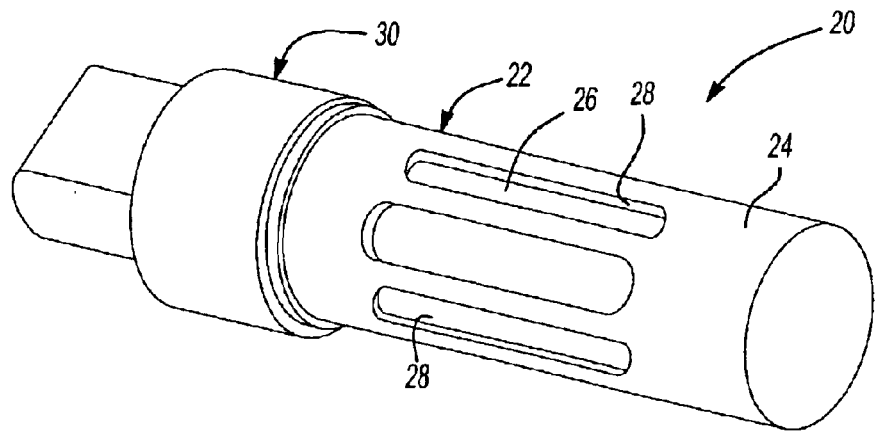
FIG. 1 schematically illustrates an example fuel sensor designed according to this invention.

FIG. 1 diagrammatically shows a fuel sensor 20 having a capacitor 22 that is used to gather information regarding the electrical properties of a fuel mixture. The illustrated example is particularly well suited for use within a vehicle fuel supply system. The capacitor 22 includes a first electrode 24 and a second electrode 26. In the illustrated example, the electrodes are generally cylindrical in shape with the outer electrode 24 generally surrounding the inner electrode 26. In one example, the outer electrode 24 is the anode while the inner electrode 26 is the cathode of the capacitor 22.

A plurality of openings 28 through the outer electrode 24 allow the fuel to flow through spacing between the electrodes 24 and 26. The size and shape of the openings 28 depend upon the needed fuel flow rate and the desired capacitor function. Increased hole size corresponds to decreased capacitance. Those skilled in the art who have the benefit of this description will be able to select the best configuration to meet the needs of their situation.

The fuel between the electrodes acts as at least one dielectric of the capacitor 22. By appropriately controlling the capacitor 22, the permittivity and conductivity of the fuel mixture is determined to provide an indication of the contents of the fuel mixture. It is known how to use capacitors to make such determinations. Such information can then be used in a conventional fashion to control a fuel supply system of a vehicle as needed.

Figure 2:
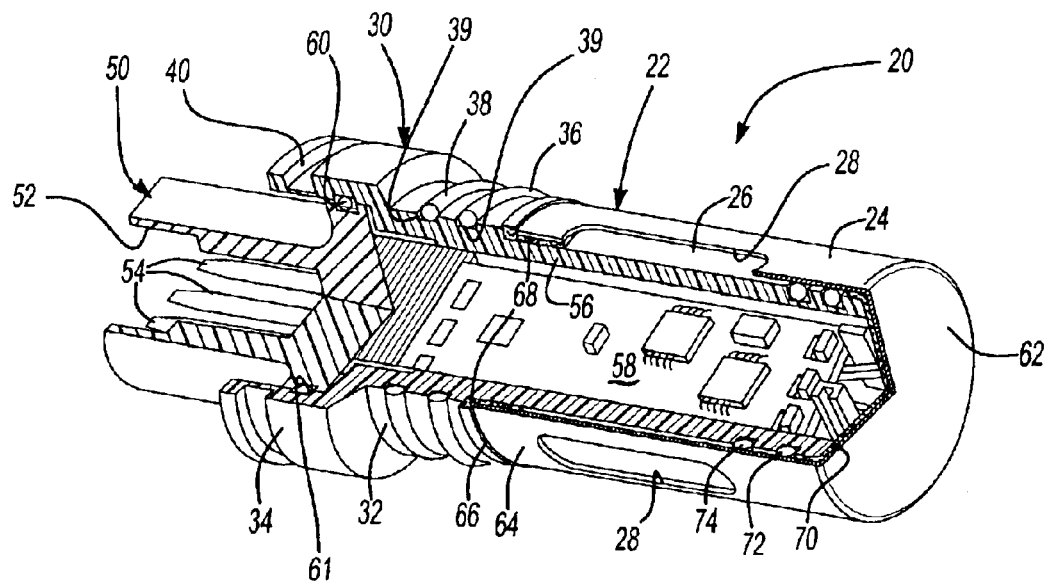
FIG. 2 is a partially cut-away, schematic illustration of selected components of the embodiment of FIG. 1.
Figure 3:
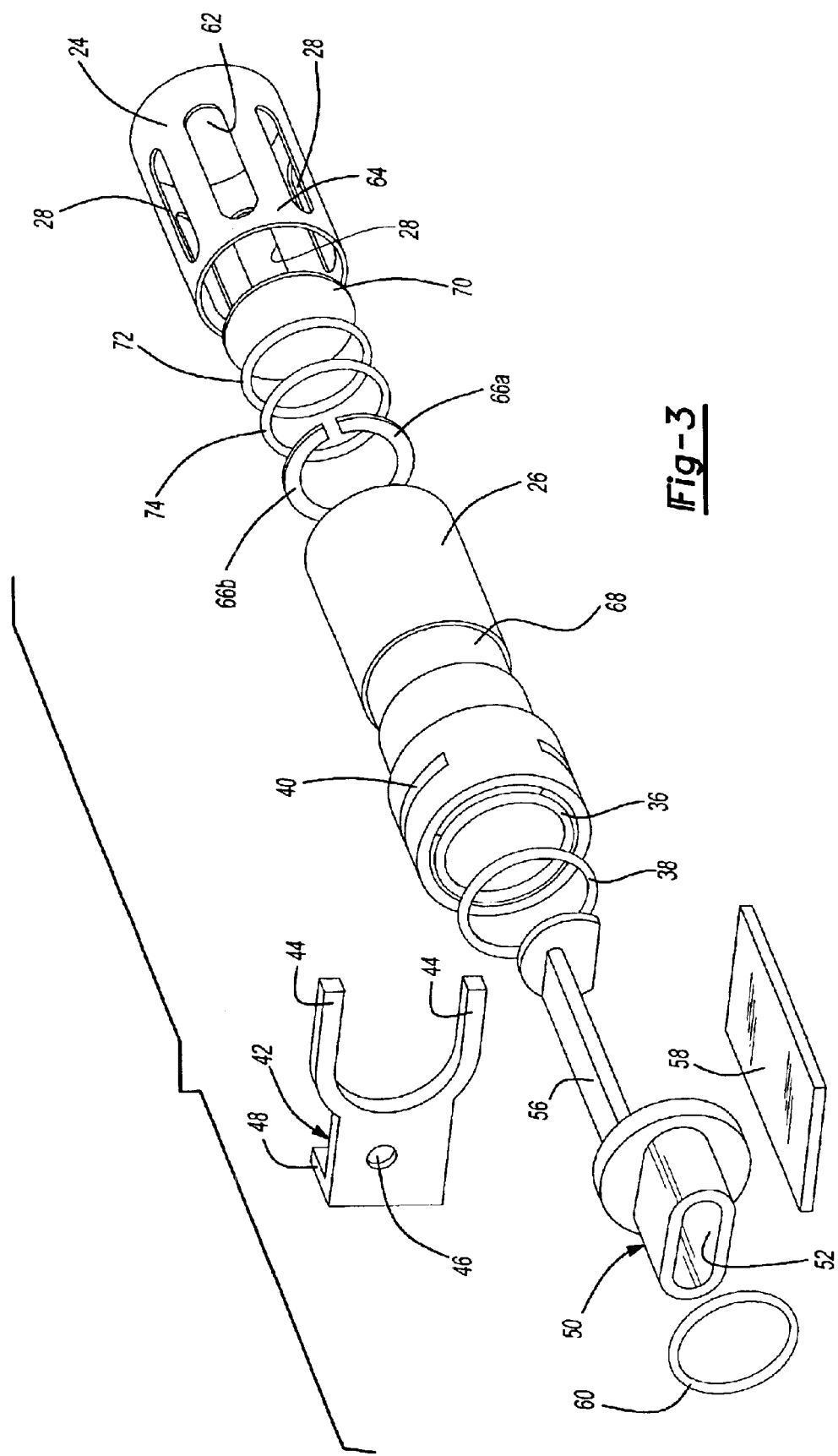
FIG. 3 is a schematic, exploded view of the embodiment of FIG. 2.

Referring to FIGS. 1–3, the fuel sensor 20 includes a mounting portion 30 that is adapted to be secured to a selected portion of a fuel supply system (not illustrated). In this illustrated example, the mounting portion 30 is formed integrally with and made of the same material as the inner electrode 26. One advantage of this invention is that it is readily adapted to be associated with any convenient portion of a fuel supply system. For example, a fuel sensor designed according to this invention may be associated directly with a fuel rail, fuel line, fuel pump or a fuel tank. By incorporating the inventive fuel sensor into a fuel rail, the fuel content information can be determined in close proximity to the fuel injectors, which has advantages for more accurately controlling the fuel supply system responsive to the detected fuel content. Placing a sensor in close proximity to the fuel injectors provides better measurements of actual fuel content at the point of injection.

The illustrated example of FIGS. 1–3 has a plug-in configuration so that the sensor 20 can be plugged into a connector or a corresponding opening in a selected portion of the fuel supply system, such as the fuel rail. Other arrangements are possible within the scope of this invention such as having threads on the mounting portion 30 so that the sensor is threadingly received into a corresponding portion of the fuel supply system. Still other embodiments (including, but not limited to, the examples discussed below and shown in the other figures) are also within the scope of this invention. Those skilled in the art who have the benefit of this description will be able to decide the best strategy for incorporating the inventive sensor arrangement into their particular system requirements.

The plug-in style of the illustrated example of FIGS. 2 and 3 includes a smaller diameter portion 32 of the mounting portion 30 having a nominal outside dimension. This smaller diameter portion 32 is adapted to be received within the corresponding opening on the appropriate portion of the fuel supply system. A larger diameter portion 34 is adapted to be received against an outside surface, such as a boss, provided on the corresponding portion of the fuel supply system. O-rings 36 and 38 are supported on grooves 39 on the smaller diameter portion 32 to provide a seal that withstands the pressures typically present in a vehicle fuel supply system. Redundant O-rings are used in this example to ensure no loss of the sealing effect during the lifetime of the sensor.

In the illustrated example, the larger diameter portion 34 includes a surface contour 40 that cooperates with a retainer element 42 for securing the sensor 20 in place at the desired location in the fuel supply system. The particularly illustrated example includes a slot 40 but other variations, irregularities or contours on the mounting portion 30 may accommodate a variety of retaining elements for securing the fuel sensor in place as needed.

The retainer member 42 best shown in FIG. 3 is a clamping bracket that preferably is crimped to the mounting portion 30 of the sensor 20 after the arms 44 of the bracket 42 are received through the corresponding slots 40 on the mounting portion 30. An opening 46 in an extension on the bracket 42 allows a bolt or screw to be appropriately secured to the corresponding portion of the fuel supply system when the bracket 42 and sensor 20 are appropriately positioned The illustrated arrangement allows for the bracket 42 to apply a force on the sensor 20 that urges the sensor into the corresponding portion of the fuel supply system. A protrusion 48 preferably extends in a direction parallel to the sensor body as the latter is received into the fuel supply system. When the protrusion 48 comes in contact with a corresponding mounting surface, it creates a moment about the contact point on the mounting surface. The forces applied onto the bracket 42 are transferred through the bracket to the tangent of the arc on the clamp surface forcing the sensor 20 into the corresponding mounting hole. Accordingly, a bracket designed as shown in the illustrated example facilitates firmly seating the sensor 20 against a mating surface such as a boss on a chosen portion of the fuel supply system so that it does not move from a desired position.

A connector portion 50 is partially received within the inner electrode 26 and supports the electronics of the sensor. In the illustrated example, the connector portion 50 is a plastic piece that has an opening 52 at one end for making an electrical connection between conductive terminals 54 supported within the opening 52 and other electrical components. Depending on the electronics of the vehicle fuel supply controller, the configuration of the terminals 54 and the connector opening 52 may be designed in a variety of ways. In one example, a first terminal 54 couples the sensor to ground, a second terminal 54 couples the sensor to a power supply and a third terminal facilitates fuel content signal communication.

The connector portion 50 includes a body section 56 that is adapted to support an electronics substrate 58. The sensor electronics may include a printed circuit board, a microprocessor, an ASIC or a combination of two or more of those, depending on the needs of a particular situation. The system electronics of one example sensor and their function will be more fully described below.

An O-ring 60 is supported in a groove 61 on the connector portion 50 for sealing off an interface between the connector portion 50 and the inside of the mounting portion 30. Such a seal prevents contamination from outside the sensor. In one example, the connector portion 50 is snap fit within the connector portion 30 so that the electronics are held securely within the inner electrode 26.

The outer electrode 24 in this example has a closed end 62 and an open end 64. An isolating member 66 is received on a reduced diameter portion 68 of the inner electrode 26. The isolating member 66 is made from an electrically insulating material to provide appropriate isolation between the electrodes 24 and 26. For ease in assembly, the example isolating member 66 has two semi-circular portions 66A and 66B that together surround the portion 68 of the inner electrode 26.

In the illustrated example, the open end 64 preferably is crimped onto the isolating member 66 so that the outer electrode 24 is secured around the outside of the inner electrode 26. Such an arrangement is particularly advantageous because it provides an economical manner of manufacturing a sensor designed according to this invention. Additionally, securing the outer electrode 24 to the inner electrode 26 using a crimp prevents any movement of the outer electrode 24 relative to the inner electrode 26 during the life of the sensor so that there are no corresponding changes to the capacitance and conductance of the sensor system.

The portion of the outer electrode 24 near the end 62 is electrically isolated from the inner electrode 26 by an isolating member 70. In the illustrated example, the isolating member 70 comprises a disk of an electrically insulating material that is received about the open end of the inner electrode 26 within the closed end of the electrode 24. In one example, the isolating member 70 is inserted into the outer electrode 24 prior to the outer electrode being received over the inner electrode 26. A set of O-rings 72 and 74 also electrically isolates the electrodes from each other.

Additionally, the O-rings 72 and 74 are received about the outside of the inner electrode 26 to seal off the open end of the inner electrode 26 and the electronics supported within the inner electrode from the fuel mixture that flows through the openings 28 in the outer electrode 24. The illustrated example includes redundant O-rings 72 and 74 to ensure a total seal throughout the lifetime of the sensor.

The electronics substrate 58 in the illustrated example is supported within the inner electrode 26. The example substrate 58 is a PCB that includes a plurality of openings 82 that receive ends of the conductors 54 as best appreciated from FIGS. 4 and 5. The conductors 54 are supported on the connector portion 50 so that at least a portion of the conductors lie in the same plane as the substrate 58. As best appreciated from FIG. 5, the conductors are bent slightly and then soldered to the substrate 58 to make the appropriate electrical connections. In the illustrated example, selective soldering can be used, which reduces the likelihood of problems associated with hand soldering techniques. In one example, a spacing between the ends of the conductors 54 received within the openings 82 is approximately 3 millimeters to enhance the manufacturing economies associated with making a sensor designed according to the illustrated embodiment.

Near the opposite end of the substrate 58, a plurality of openings 84 receive heat stake posts 86 that are formed as part of the body 56 of the connector portion 50. A conventional heat staking operation is used to secure the substrate 58 to the posts 86 so that the substrate 58 is positioned securely on the body 56.

In the illustrated example, electrical connections are made with the inner and outer electrodes of the capacitor 22 using conductive springs made from beryllium copper, which preferably are gold plated to minimize the possibility for corrosion and loss of electrical contact. Referring to FIGS. 4–7, the illustrated substrate 58 includes an opening 90 in a central portion of the substrate. A post 92 on a first spring contact 94 is received through the opening 90. Connecting portions 96 and 98 extend outwardly away from and beyond the edges of the substrate 58 so that the connector portions 96 and 98 make electrically conductive, mechanical contact with the inner surface on the inner electrode 26. The bias of the spring 94 maintains the necessary electrical contact.

Near the end of the substrate 58 furthest from the opening 52 a post 100 of another contact spring 102 is received through an opening 104. The contact spring 102 includes electrical contact portions 104 and 106 that directly contact the interior surface on the outer electrode 24. The electronics on the substrate 58 are appropriately wired so that electrical contact between the electronics and the inner and outer electrodes for operating the capacitor 22 is accomplished using the springs 94 and 102.

Figure 4:
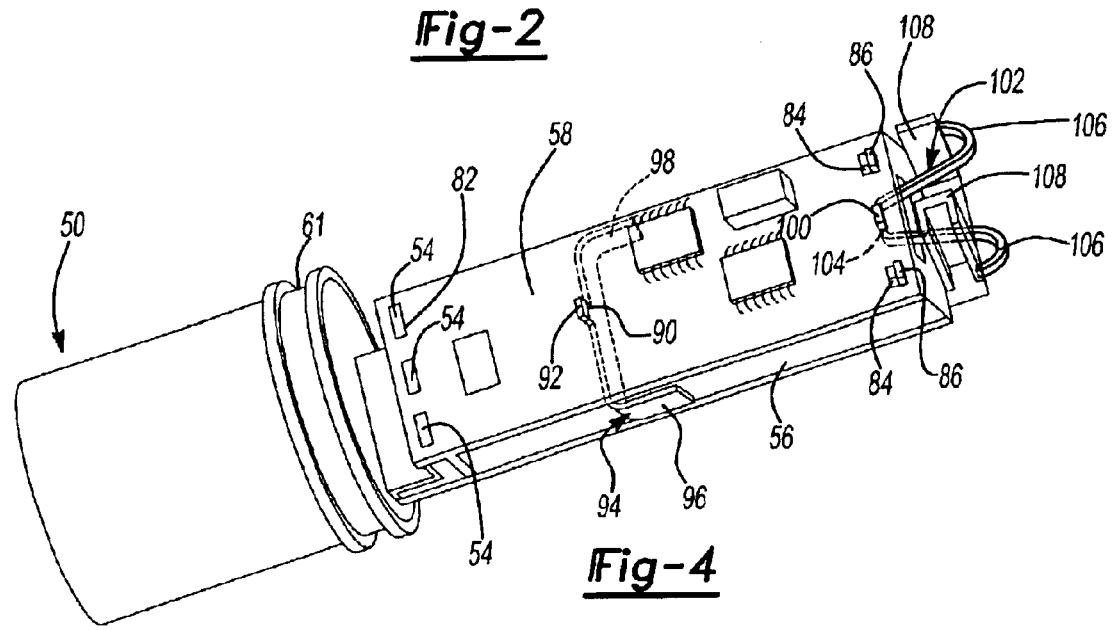
FIG. 4 schematically illustrates selected portions of the embodiment of FIG. 2 showing selected details of an example arrangement for supporting electronics within the fuel sensor.

As best appreciated in FIGS. 4 and 7, the spring 102 includes generally hook-shaped portions extending away from opposite sides of the post 100. These hook shaped portions are received about posts 108 formed as part of the body 56 of the connector portion 50. The resiliency of the spring 102 secures the spring in position about the posts 108 in cooperation with the post 100 being received through the opening 104. At the same time, the connector portions 104 and 106 extend away from the posts 108 a distance sufficient to make electrical contact with the outer electrode 24.

Figure 8:
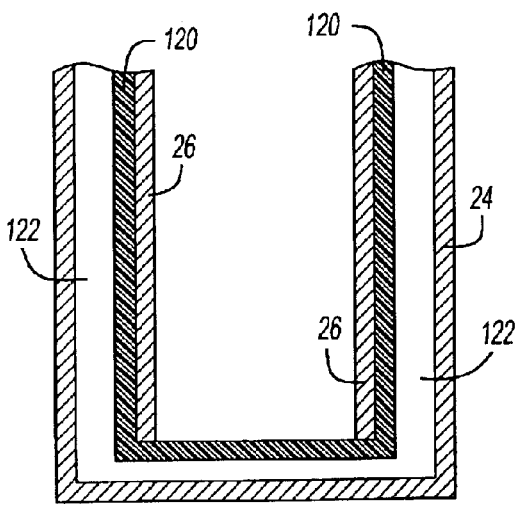
FIG. 8 is a cross-sectional illustration of selected portions of a fuel sensor designed according to this invention showing an alternative electrical isolation arrangement.

FIG. 8 illustrates selected portions of an alternative arrangement of a sensor assembly designed according to this invention. In this example, instead of having independent isolating members 66 and 70, the inner electrode 26 is overmolded with a suitable material 120 that provides the insulating barrier for isolating the inner electrode 26 from the outer electrode 24. As can be appreciated from FIG. 8, the fuel mixture flows through the spacing 122 between the electrodes 26 and 24. Accordingly, the material selected for overmolding the inner electrode 26 to form the insulating barrier 120 must be chosen to be compatible with the anticipated range of fuel mixtures in a particular fuel supply system. In one example, a material supplied by Dupont known as Vespel ST2030 was chosen. Those skilled in the art who have the benefit of this description will be able to determine what materials will best suit the needs of their particular situation.

In one such example, the mounting portion 30 is formed integrally with the outer electrode 24 rather than the inner electrode 26 (as shown in the example of FIGS. 2 and 3). The insulating layer 120 is supported on the mounting portion 30 and the inner electrode 26 is supported in the insulating layer 120.

Figure 9:
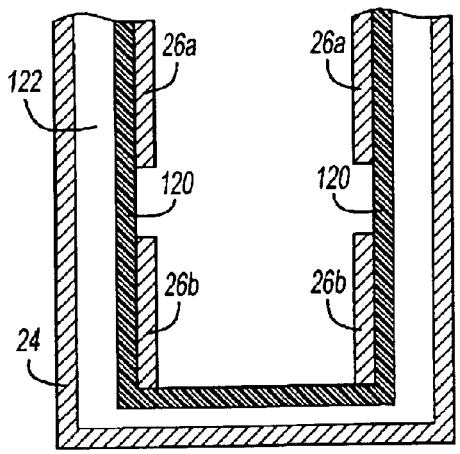
FIG. 9 is a cross-sectional illustration similar to that of FIG. 8 showing an alternative arrangement particularly well suited for measuring the characteristics of diesel fuel.

FIG. 9 illustrates another example where the inner electrode 26 is supported on an insulating layer 120 that is received within the outer electrode 24 and maintains the necessary amount of spacing 122 to allow fuel flow between the electrodes 24 and 26. In the example of FIG. 9, two separate inner electrodes 26A and 26B are provided. Such an arrangement is particularly useful for diesel fuel systems. In this example, the first inner electrode 26A is used for sensing the diesel fuel content while the second electrode 26B is used for sensing water. Accordingly, utilizing two separate inner electrodes allows a sensor assembly designed according to this invention to provide information necessary for making the unique determinations associated with monitoring the quality of diesel fuel.

Figure 10:
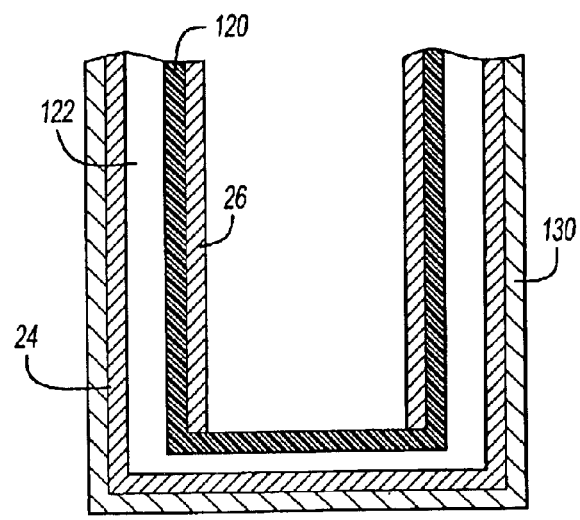
FIG. 10 is a partial cross-sectional illustration of selected portions of a fuel sensor designed according to this invention that includes a fuel filter.

The inventive sensor arrangement has many advantages including the ability to be readily incorporated into a variety of portions of a fuel supply system. One example implementation of this invention is schematically shown in FIG. 10, which is a cross sectional illustration. In this example, fuel filter material 130 is received around the outer electrode 24. Accordingly, the fuel sensor assembly 20 in this example also provides the fuel filter function necessary within a fuel supply system. Although schematically illustrated as an outside addition to the outer electrode 26, the fuel filter components themselves serve as the outer electrode in another example.

Such integration of components within the fuel supply system enhances the economies of the overall system and the individual components. By eliminating the need for a separate fuel sensor and fuel filter, the inventive arrangement allows for faster assembly, less connections to be made with a fuel rail or other fuel system component and minimizes the labor required during assembly, for example.

FIG. 11 schematically illustrates another example fuel sensor arrangement designed according to this invention. In this example, the sensor 20 is incorporated into a portion of the fuel rail 132. The sensor is modified in that the corresponding portion of the fuel rail 132 operates as the outer electrode of the capacitor 22'. In this example, the inner electrode 26' is received within the corresponding portion of the fuel rail 132, which acts as the outer electrode. In this example, the fuel rail portion 132 is the cathode while the inner electrode 26' is the anode of the capacitor 22'. The fuel rail portion 132 operates as the cathode in this example because it is shunted to ground. Other than such a reversed polarity, the capacitor 22' operates in the same manner as the capacitor 22.

Conventionally configured fuel conduit connectors 134 are adapted for connecting with the remaining portions of the fuel rail.

FIG. 12 illustrates another alternative arrangement where a separate housing 150 supports the sensor 20 in a desired location relative to the fuel supply system on the vehicle. The illustrated example includes an opening 152 that receives the capacitor 22 of the sensor 20 and an insert 154 that sealingly secures the sensor in place. In such an arrangement, the sensor 20 can be secured to the housing 150 in a variety of manners, depending on the particular material selected to form the housing 150 and the insert 154. In one example, adhesive is used, in another example a crimping operation secures the sensor in place. In another example, a clamp or bracket similar to the securing member 40 is used.

The housing 150 includes a first connector 156 that allows fuel flow into a body portion 158 of the housing 150 where the fuel encounters the sensor 20. The fuel then flows out another connector 160 as it continues along in the appropriate portion of the fuel supply system.

As can be appreciated in FIG. 13, in one example, the housing 150 includes a cap 162 that is received over one end of the body portion 158 to close off that portion of the housing that will receive fuel during system operation. The cap 162 in the illustrated example includes a mounting portion 164 that is adapted to be secured to an appropriate portion of the fuel supply system or a convenient support surface on the vehicle.

Depending on the chosen material, the housing 150 may be used as the outer electrode of the capacitor.

Having described the various components of several example embodiments of a fuel sensor designed according to this invention, attention will now be turned to the electronics used to operate the sensor. The general principles of making capacitance and conductance measurements are known. As will become apparent, the inventive sensor uses conventional measuremnt principles but also includes novel features distinguishing the inventive arrangement from prior sensors.

Figure 14:
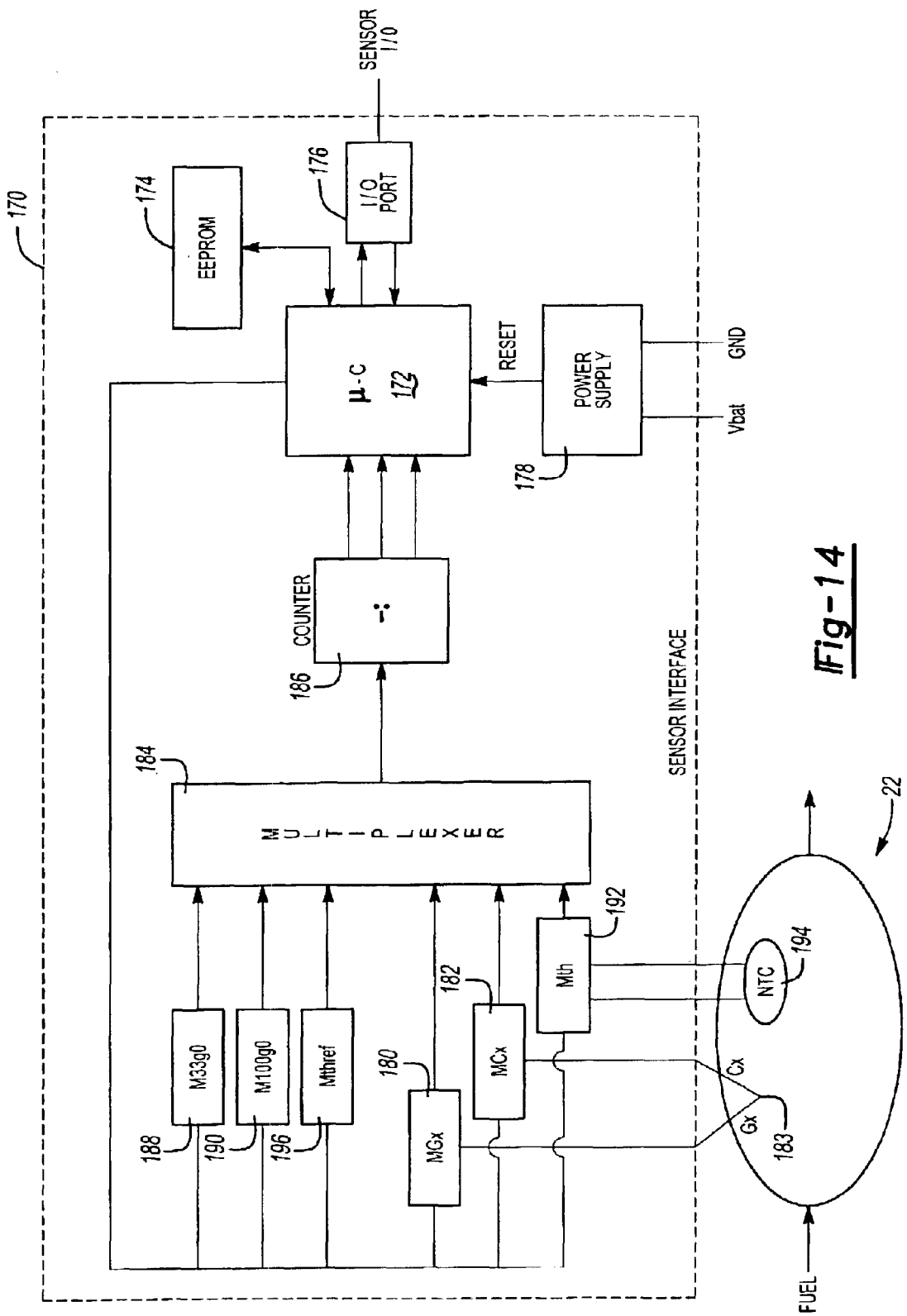
FIG. 14 schematically illustrates example electronics used to operate a fuel sensor designed according to this invention.

FIG. 14 schematically illustrates the sensor capacitor 22 and electronics 170 for operating the sensor. A microprocessor 172 is suitably programmed to gather the capacity, temperature and conductivity information obtained by the sensor and to compare that information to data stored in the ROM of the controller 172 to make a fuel mixture content determination. Calibration parameters of the sensor are stored in the EEPROM 74. In one example, the ROM of the controller 172 includes a look up table of a plurality of predetermined sensor values corresponding to specific known fuel mixtures. The microprocessor 172 is programmed to utilize that information and provide an output through a conventional communication port 176 to be used by the engine controller or other fuel supply controller that is responsible for operating the timing and the amount of fuel flow through fuel injectors to achieve the desired response to the fuel mixture content determinations. In one example, the sensor output is a frequency and negative pulse width modulated signal. A conventional power supply 178 powers the microprocessor 172.

One unique feature of this invention is the use of a single capacitor 22 to make the conductivity and permittivity measurements of the fuel mixture. Two different oscillators 180 and 182 are selectively coupled with the capacitor 22 to make the two separate determinations (i.e., conductivity and capacity). The inventive arrangement includes a single mechanical connection 183 between the capacitor 22 and the oscillators 180 and 182. Instead of switching the connection to the capacitor 22, the example implementation of this invention includes switching the oscillator outputs, in such a case parasitic capacitance does not influence the capacity to measure.

The electronics 170 include a multiplexer 184 that receives the output of the oscillators 180 and 182. In one example, one of the oscillators operates in the megahertz range while the other operates in a kilohertz range. Because of these relatively high frequencies, a counter 186, which acts as a divider, is provided between the multiplexer 184 and the microprocessor 172 so that the microprocessor is capable of handling the signal information from the oscillators. Although schematically shown as separate "components," the various portions of FIG. 14 or 15 may be implemented using a suitably programmed microprocessor, for example. The illustrated divisions are for discussion purposes, only.

The inventive arrangement includes operating the oscillators 180 and 182 at different frequencies and independent from each other so that the capacitor 22 is used in two different modes, depending on which oscillator is activated.

To compensate for component drifting and aging, reference oscillators 188 and 190 are provided. In one example, the reference oscillator 188 is set to provide an indication of a fuel alcohol content at a lower end of an expected spectrum. The oscillator 190 is set to provide an indication corresponding to a fuel alcohol content at an opposite end of an expected spectrum. In one example the reference capacitor 188 corresponds to a ten percent alcohol content while the reference capacitor 190 corresponds to an eighty percent alcohol content. The reference oscillators preferably are selected to remain fixed so that they are not affected over the lifetime of the sensor assembly.

As known, another factor included when making a fuel content determination using capacity and conductivity is the temperature of the fuel mixture. In one example sensor designed according to this invention, a thermistor or NTC device is used to gather the fuel temperature information. One advantageous feature of the inventive arrangement is the ability to support the thermistor device on the connector portion 50 to maintain minimal statistical spread in temperature information. One example includes thermal grease to wet the surface of the sensor body and to couple it to the thermistor for maximum convective and radiative heat transfer to the thermistor device. It is preferred not to leave any spacing between the thermistor and the sensor body without thermal grease to avoid variable or extended response to a change in the fuel temperature.

In one example, the thermistor device is held in place in a pocket molded on a corresponding portion of the connector portion 50. The pocket holds the thermistor at a desired spacing from the substrate 58. The electrical leads of a thermistor can be soldered to appropriate portions of the electronics supported on the substrate 58.

After assembly, the thermistor preferably has grease supplied to the area around the pocket on the connector portion 50 and installed into the sensor body. The thermally conductive grease allows for pressure compensation inside of the sensor. Because the sensor in one example is sealed with O-rings, pressure differentials may have to be vented out from the inside of the sensor. A tapered hole molded in the connector portion 50 extending from the outside of the connector assembly into the pocket for supporting the thermistor accomplishes this in an effective manner in one example. The thermally conductive grease can be inserted into the hole to then fill the cavity around the thermistor to accomplish wetting the surface of the thermistor and the sensor body in the appropriate region. Any remaining grease inside of the hole seals the hole but is soft enough to allow pressure to escape by pushing the grease forward or backward inside the hole as pressure rises or falls inside the sensor. The resulting arrangement provides a sensor that remains sealed and compensates for changes in pressure by allowing changes in volume resulting from at least some of the grease moving within the hole.

The illustrated example arrangement includes another oscillator 192 that is coupled with a thermistor 194 that obtains fuel mixture temperature information. A reference oscillator 196 is chosen to provide calibration information to compensate for drift or aging of the oscillator 192 over time.

The use of oscillators in combination with capacitors and thermistors for obtaining the necessary information regarding the fuel mixture content are known. One advantageous difference of this invention is that a single capacitor is used in two modes and only a single mechanical connection 183 between the capacitor 22 and the oscillators 180 and 182 simplifies the overall assembly and makes it more economical.

The microprocessor 172 preferably is programmed to selectively switch between the oscillators 180 and 182 to make the appropriate conductivity or capacity measurements. The example of FIG. 15 includes electronic switches 200 and 202 that are selectively operated by the microprocessor 172 to achieve the desired oscillator operation to obtain the desired measurement. Similarly, the microprocessor 172 controls electronic switches 204 and 206 to select either of the reference oscillators 188 and 190.

Figure 15:
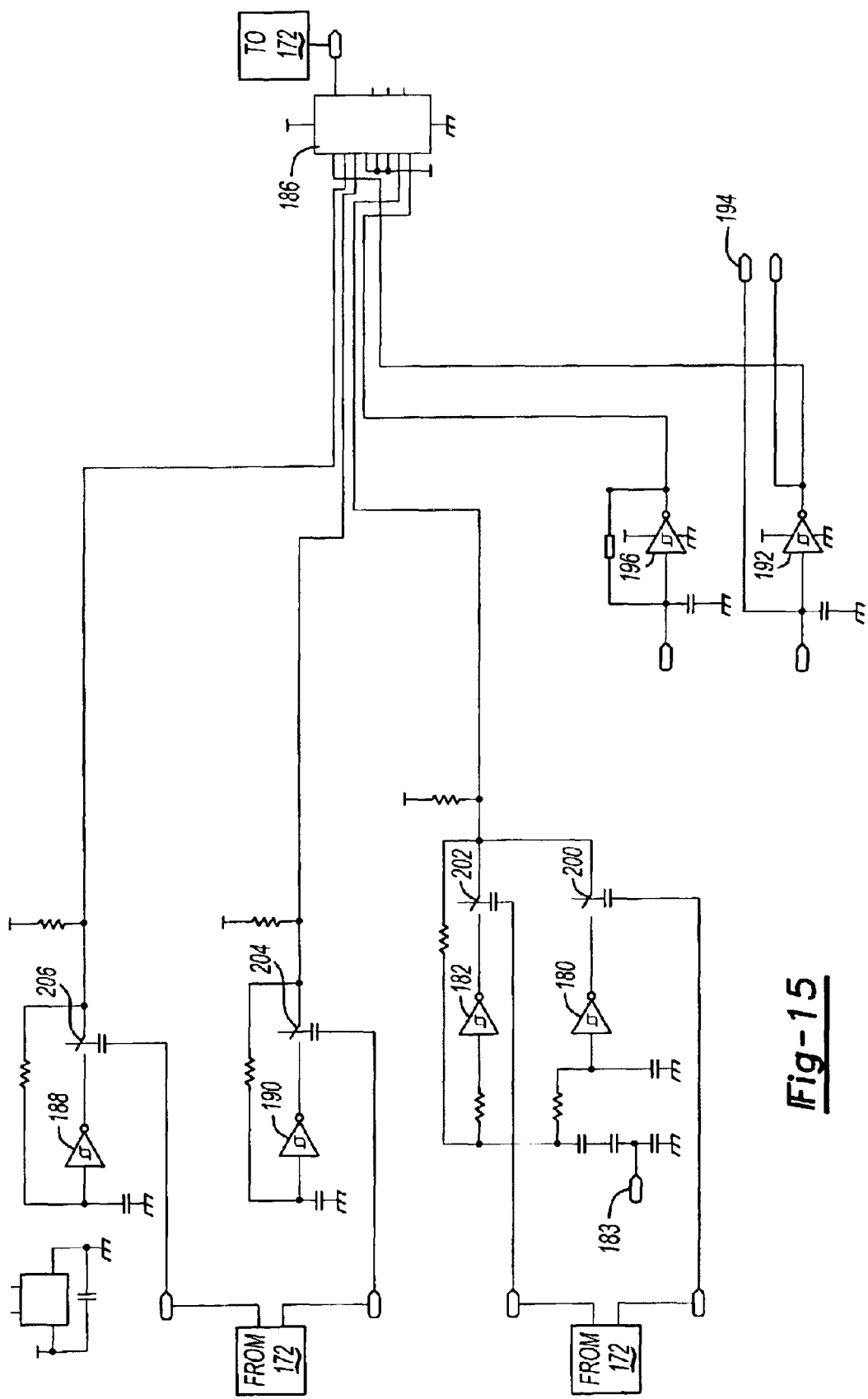
FIG. 15 schematically illustrates, in somewhat more detail, an example implementation of electronics for operating a fuel sensor designed according to this invention.

The arrangement of electronics for operating a sensor designed according to this invention can take a variety of forms. The example of FIG. 15 is one particular implementation of the overall inventive strategy. Those skilled in the art who have the benefit of this description will be able to select from commercially available electronic components or to specially design hardware and software to meet the needs of their particular situation.

Figure 16:
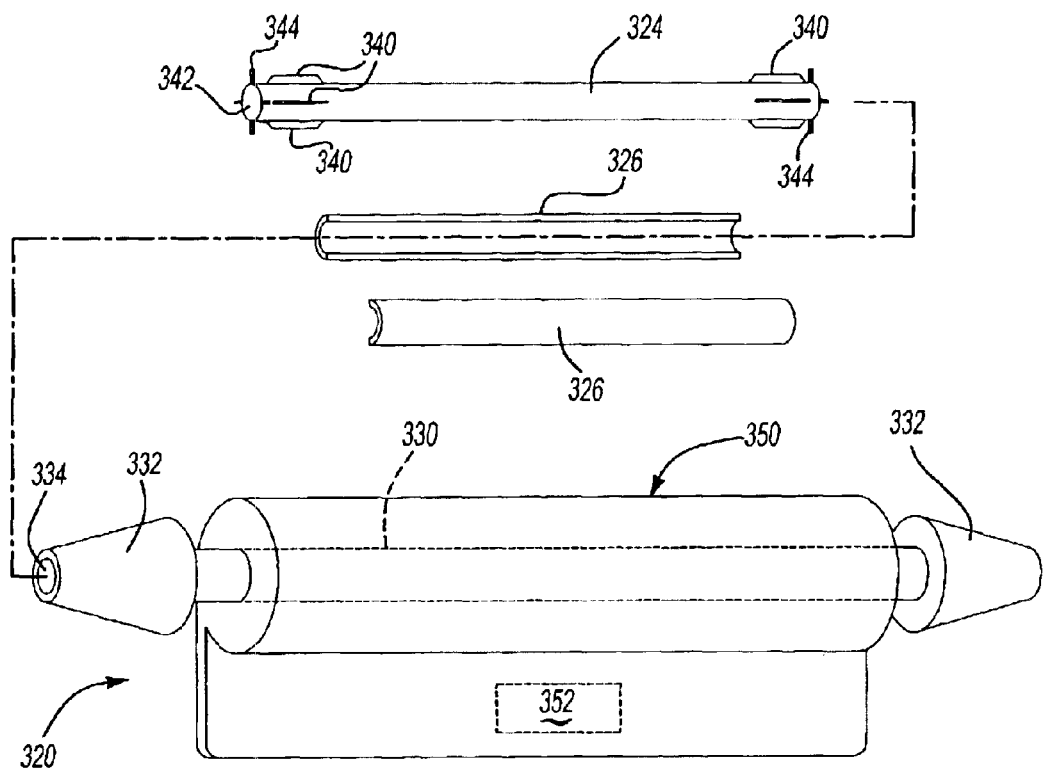
FIG. 16 schematically illustrates another example fuel sensor arrangement designed according to this invention that is particularly adapted to be incorporated in a fuel line.

FIG. 16 illustrates another example embodiment of a fuel sensor designed according to this invention. This example is particularly well suited to be incorporated in a fuel line. The sensor 320 includes a capacitor 322 having an inner electrode 324 and an outer electrode 326. The inner electrode 324 is received within a nonconductive tube 330. In one example, the nonconductive tube 330 is made using the Vespel ST2030 material available from Dupont.

The tube 330 preferably extends a selected distance and has conventional fuel line connector ends 332 with an opening 334 extending through the tube 330 so that the fuel from the fuel line flows through the tube 330. The inner electrode 324 is received within the opening 334. A plurality of ribs 340 on an outside of the inner electrode 324 position the inner electrode 324 coaxially with the tube 330. Extensions 344 secure the electrode 324 in place axially by being bent over the ends of the tube 330 in one example.

The outer electrode 326 in the illustrated example comprises two separate electrode portions that are each received against the outside of the tube 330. A housing 350 supports the outer electrode portions 326 such that they are secured in a fixed position relative to the outside of the tube 330.

The housing 350 also houses electronics 352 for operating the fuel sensor 320. One advantage of this embodiment is that the electrical connections between the electronics 352 and the capacitor 322 occur only with the outer electrodes 326 which are completely isolated from the fuel mixture. Accordingly, all electrical connections are completely isolated from the fuel mixture and no special sealing arrangement is required.

Figure 17:
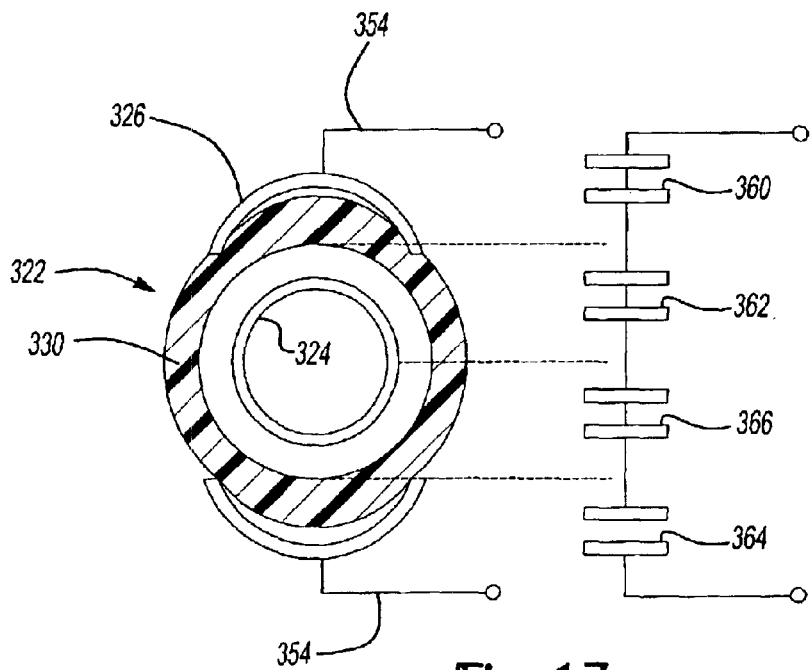
FIG. 17 schematically illustrates a feature of the embodiment of FIG. 16.

FIG. 17 schematically illustrates the operation of the fuel sensor 320. As can be appreciated from the drawing, the arrangement of an insulating tube 330 between the two outer conductors 326 and the inner conductor 324 effectively provides four capacitors in series. The tube 330 acts as a first dielectric between a first one of the outer electrodes 326 and the inner electrode 324. This capacitor is represented by the capacitor 360. The fuel flowing within the tube 330 has a significantly different dielectric constant compared to the material of the tube 330 and, therefore, effectively is a second capacitor between the outer electrode 326 and the inner electrode 324. This capacitor is shown at 362.

The same is true for the other outer electrode 326. This relationship is schematically shown by the capacitor 364 and 366. Accordingly, with such a fuel sensor, the electronics are preferably programmed to make the permittivity and conductivity measurements based upon a model of four, in-series capacitors. Because the dielectric constant of the material selected for the tube 330 typically is much higher than that of the fuel mixture, the influence of that material on the conductivity and permittivity measurements can be readily handled with suitable programming or arrangements of the electronics of the sensor 320.

A variety of example fuel sensors designed according to this invention have been disclosed. Variations and modifications to the disclosed examples may become apparent to those skilled in the art that do not necessarily depart from the basis of this invention. The scope of legal protection given to this invention can only be determined by studying the following claims.

We claim:

1. A fuel sensor, comprising:
    a capacitor having a first, generally cylindrical electrode and a second electrode at least partially surrounding the first electrode, the electrodes being spaced apart such that the fuel flows between the electrodes;
    a first oscillator selectively coupled with the capacitor to provide an indication of the capacitance of the capacitor when the fuel is between the electrodes;
    a second oscillator selectively coupled with the capacitor to provide an indication of the conductance of the capacitor when the fuel is between the electrodes; and
    a controller that operates the first and second oscillators with the capacitor to obtain the respective indications;
    a temperature indicator that communicates fuel temperature information to the controller, the controller uses the temperature information, the capacitance indication and the conductance indication to determine the contents of the fuel; and
    a memory portion having a plurality of predetermined values indicative of fuel content and wherein the controller determines the fuel content from among the predetermined values based upon the temperature information, the capacitance indication and the conductance indication.

2. A fuel sensor, comprising:
    a capacitor having a first, generally cylindrical electrode and a second electrode at least partially surrounding the first electrode, the electrodes being spaced apart such that the fuel flows between the electrodes;
    a first oscillator selectively coupled with the capacitor to provide an indication of the capacitance of the capacitor when the fuel is between the electrodes;
    a second oscillator selectively coupled with the capacitor to provide an indication of the conductance of the capacitor when the fuel is between the electrodes; and,
    a controller that operates the first and second oscillators with the capacitor to obtain the respective indications, wherein the first electrode is hollow and the controller and the oscillators are supported within the first electrode.

3. The sensor of claim 2, including a single, uninterrupted mechanical connection between both of the first and second oscillators and the capacitor, the controller selectively operating a selected one of the oscillators with the capacitor to obtain a desired one of the indications.

4. The sensor of claim 3, including electronic switches associated with each of the oscillators that are responsive to the controller to operate the selected oscillator with the capacitor.

5. The sensor of claim 2, including a connector portion having a body that supports a substrate on which the oscillators and the controller are supported, the body being received in the first electrode and a terminal support that is external to the first electrode and is adapted to make an electrical connection between the sensor and another electronic component supported on a vehicle.

6. The sensor of claim 2, including a substrate that supports the oscillators and the controller and including at least one conductive spring that is mechanically supported between the substrate and a corresponding one of the electrodes.

7. The sensor of claim 6, wherein the spring comprises a post that is at least partially received through a corresponding opening on the substrate and at least one conductive extension that is biased into contact with the corresponding electrode.

8. The sensor of claim 7, wherein the spring includes two conductive extensions that are biased into electrically conductive contact with the corresponding electrode.

9. The sensor of claim 6, wherein the spring comprises copper beryllium.

10. A fuel sensor, comprising:
    a capacitor having a first, generally cylindrical electrode and a second electrode at least partially surrounding the first electrode, the electrodes being spaced apart such that the fuel flows between the electrodes;
    a first oscillator selectively coupled with the capacitor to provide an indication of the capacitance of the capacitor when the fuel is between the electrodes;
    a second oscillator selectively coupled with the capacitor to provide an indication of the conductance of the capacitor when the fuel is between the electrodes; and
    a controller that operates the first and second oscillators with the capacitor to obtain the respective indications, wherein the second electrode is generally cylindrical having an open end and a closed end, the open end being received about a selected portion of the first electrode.

11. The sensor of claim 10, wherein the open end of the second electrode is crimped onto a selected portion of the first electrode.

12. The sensor of claim 10, including an isolating member between the open end of the second electrode and the first electrode and wherein the isolating member comprises two semicircular portions received on the selected portion of the first electrode.

13. The sensor of claim 10, including at least one O-ring between the first and second electrodes, the O-ring sealing electrically isolating the electrodes from each other and providing a fluid seal preventing the fuel from contacting selected portions of the sensor.

14. The sensor of claim 2, including a connector portion that is adapted to be received directly into a selected location on a vehicle fuel supply system.

15. The sensor of claim 2, including a housing that is adapted to be in fluid communication with a vehicle fuel supply system and wherein at least the first electrode of the capacitor is received within the housing.

16. The sensor of claim 15, wherein the housing comprises a non-conductive material and the first and second electrodes are received at least partially within the housing.

17. A fuel sensor, comprising:
    a capacitor having a first, generally cylindrical electrode and a second electrode at least partially surrounding the first electrode, the electrodes being spaced apart such that the fuel flows between the electrodes;
    a first oscillator selectively coupled with the capacitor to provide an indication of the capacitance of the capacitor when the fuel is between the electrodes;
    a second oscillator selectively coupled with the capacitor to provide an indication of the conductance of the capacitor when the fuel is between the electrodes; and
    a controller that operates the first and second oscillators with the capacitor to obtain the respective indications, wherein the second electrode comprises at least a selected portion of a fuel rail.

18. A fuel sensor, comprising:
    a capacitor having a first, generally cylindrical electrode and second electrode at least partially surrounding the first electrode, the electrodes being spaced apart such that the fuel flows between the electrodes;

a first oscillator selectively coupled with the capacitor to provide an indication of the capacitance of the capacitor when the fuel is between the electrodes;

a second oscillator selectively coupled with the capacitor to provide an indication of the conductance of the capacitor when the fuel is between the electrodes; and a controller that operates the first and second oscillators with the capacitor to obtain the respective indications, including fuel filter material supported on the second electrode.

19. A fuel sensor, comprising:

a capacitor having a first, generally cylindrical electrode and a second electrode at least partially surrounding the first electrode, the electrodes being spaced apart such that the fuel flows between the electrodes;

a first oscillator selectively coupled with the capacitor to provide an indication of the capacitance of the capacitor when the fuel is between the electrodes;

a second oscillator selectively coupled with the capacitor to provide an indication of the conductance of the capacitor when the fuel is between the electrodes; and a controller that operates the first and second oscillators with the capacitor to obtain the respective indications;

an electrically nonconductive tube adapted to be coupled in fluid communication with a vehicle fuel line and wherein the first electrode is supported within the tube with a spacing between the first electrode and the tube such that fuel flows through the tube around the exterior of the first electrode and wherein the second electrode is outside of the tube; and a single housing that supports the tube, the electrodes, the oscillators and the controller.

20. The sensor of claim 19, wherein the second electrode comprise two semi-cylindrical members secured to the exterior of the tube and wherein the oscillators are each coupled to both semi-cylindrical members, the tube isolating the fuel from any electrical energy applied to the electrodes.

21. The sensor of claim 19, wherein the first electrode includes a plurality of ribs that are received against an interior surface on the tube to maintain a desired position of the first electrode within the tube.

22. A fuel sensor, comprising:

a capacitor having a first, generally cylindrical electrode and a second electrode at least partially surrounding the first electrode, the electrodes being spaced apart such that the fuel flows between the electrodes;

a first oscillator selectively coupled with the capacitor to provide an indication of the capacitance of the capacitor when the fuel is between the electrodes;

a second oscillator selectively coupled with the capacitor to provide an indication of the conductance of the capacitor when the fuel is between the electrodes;

a controller that operates the first and second oscillators with the capacitor to obtain the respective indications; and a third electrode associated with the second electrode, the first electrode being used to gather fuel content information and the third electrode being used to gather water content information.

23. The sensor of claim 22 including an insulator supporting the first electrode and the third electrode, the insulator at least partially surrounding the first and third electrodes, respectively.

24. The sensor of claim 2, including a temperature sensor that communicates fuel temperature information to the controller.

25. The sensor of claim 24, wherein the temperature sensor is supported within one of the electrodes.

26. The sensor of claim 10, including a temperature sensor that communicates fuel temperature information to the controller.

27. The sensor of claim 26, wherein the temperature sensor is supported within one of the electrodes.

* * * * *